United States Patent
Yang et al.

(10) Patent No.: US 9,770,045 B2
(45) Date of Patent: Sep. 26, 2017

(54) PRESERVATION OF ANIMAL FEED AND HYDROLYSIS OF POLYSACCHARIDES USING AMINO ACIDS AS SALTS OR WITH ACIDS

(71) Applicant: The Board of Regents of The University of Texas System, Austin, TX (US)

(72) Inventors: Duck Joo Yang, Flower Mound, TX (US); Matthew Fiala, Hickory Creek, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/017,256

(22) Filed: Feb. 5, 2016

(65) Prior Publication Data
US 2016/0227818 A1   Aug. 11, 2016

Related U.S. Application Data

(60) Provisional application No. 62/112,252, filed on Feb. 5, 2015.

(51) Int. Cl.
| | |
|---|---|
| *A23L 1/10* | (2006.01) |
| *A23K 30/10* | (2016.01) |
| *C07H 3/02* | (2006.01) |
| *C07H 1/00* | (2006.01) |
| *A23K 10/30* | (2016.01) |
| *A23K 10/32* | (2016.01) |
| *A23K 30/00* | (2016.01) |

(52) U.S. Cl.
CPC ............. *A23K 30/10* (2016.05); *A23K 10/30* (2016.05); *A23K 10/32* (2016.05); *C07H 1/00* (2013.01); *C07H 3/02* (2013.01); *A23K 30/00* (2016.05)

(58) Field of Classification Search
CPC ........ A23K 30/10; A23K 10/30; A23K 10/32; A23K 30/30; C07H 1/00; C07H 3/02
USPC ........ 426/331, 615, 656, 658, 478, 481, 520
See application file for complete search history.

(56) References Cited

U.S. PATENT DOCUMENTS

| | | | |
|---|---|---|---|
| 8,211,689 B2 | 7/2012 | Yoshikuni | |
| 8,747,561 B2 * | 6/2014 | Tao .......................... | C13K 1/02 127/37 |
| 8,853,446 B2 | 10/2014 | McDonald, III | |

(Continued)

FOREIGN PATENT DOCUMENTS

WO    WO2013/017289    2/2013

OTHER PUBLICATIONS

Badger, P.C. 2002. Ethanol from cellulose: A general review. p. 17-21. In: J. Janick and A. Whipkey (eds.), Trends in new crops and new uses. ASHS Press, Alexandria, VA.

(Continued)

*Primary Examiner* — Helen F Heggestad
(74) *Attorney, Agent, or Firm* — Parker Highlander PLLC

(57) ABSTRACT

In some aspects, the present disclosure relates to a method of hydrolyzing a polysaccharide to obtain the corresponding saccharides using an amino acid solution. In some embodiments, the present disclosure provides a method of using an amino acid salt such as hydrogen glycine in a solution to obtain a monosaccharide such as glucose, xylose, or fructose.

16 Claims, 6 Drawing Sheets
(6 of 6 Drawing Sheet(s) Filed in Color)

(56) References Cited

U.S. PATENT DOCUMENTS

2012/0009280 A1* 1/2012 Houseman ............. A23K 40/10
 424/693
2012/0156717 A1 6/2012 Allnut et al.
2014/0041690 A1 2/2014 McDonald, III

OTHER PUBLICATIONS

Curzens and Miller, "Acid hydrolysis of bagasse for ethanol production," *Renew. Energy*, 10:285-290, 1997.
Farina, et al., "Fuel Alcohol Production from Agricultural Lignocellulosic Feedstocks," *Energy Source Part A*, 10:231-237, 1988.
Pauly and Keegstra, "Cell-wall carbohydrates and their modifications as a resource for biofuels," *The Plant Journal*, 54:559-568, 2008.
Taherzadeh and Karimi, Acid-Based Hydrolysis Processes for Ethanol From Lignocellulosic Materials: A Review. BioResources, North America, 2, Aug. 2007. Available at: <ojs.cnr.ncsu.edu/index.php/BioRes/article/view/BioRes_2_3_472_499_Taherzadeh_K_AcidHydrolysis_BioEthanol/62>. Date accessed: Oct. 30, 2014.
Wright and Powers, "Energy from Biomass and Wastes, Comparative Technical Evaluation of Acid Hydrolysis Processes for Conversion of Cellulose to Alcohol," *Energy Biomass Wastes*, 949-971, 1987.

\* cited by examiner

PRESERVATION OF ANIMAL FEED AND HYDROLYSIS OF POLYSACCHARIDES USING AMINO ACIDS AS SALTS OR WITH ACIDS

This application claims the benefit of U.S. Provisional Application Ser. No. 62/112,252, filed on Feb. 5, 2015, the entire contents of which are incorporated herein by reference.

BACKGROUND

1. Field

The present disclosure generally relates to the fields of biofuels and polysaccharide hydrolysis. More specifically, it relates to the use of amino acids as salts or with acids to hydrolyze polysaccharides and cellulosics.

2. Related Art

Cellulose is one of the most abundant materials on earth, found in every plant, tree and crop. Although it is used in some commercial processes, a vast majority of cellulose is tossed as waste in the form of corn husks, wood shavings, and other plant by-products. There are many documented attempts in the literature to utilize this waste and transform the polysaccharide in to simple sugars, which can then be fermented by yeast to produce so called bioethanol for biofuels or treated by algae to produce biodiesel for biofuels. However, there are still many problems that keep this from being commercialized. One of the biggest issues is the sturdiness of cellulose; it is very difficult to break down. There are two main methods of achieving this, inorganic acid hydrolysis and enzymatic hydrolysis, each of which has its own benefits and downfalls.

Enzymatic hydrolysis uses specialized enzymes to hydrolyze cellulose at fairly low temperatures. It can obtain high yields and enzymes cannot be easily separated from the mixture after usage. The concern with an industrial scale process using enzymes is that they have a relatively short life and must constantly be replaced—a very costly expenditure which has prevented its large scale use (Badger, 2002).

Acid hydrolysis focuses on the use of strong inorganic acids such as hydrochloric or sulfuric acid. These can be used in high concentration at relatively low temperatures (less than 80° C.) to receive high yields of sugar. However, these acids are very corrosive and require expensive alloy equipment, as well as being dangerous to workers and generate waste solution that must be treated before disposal. Additionally, for the process to be efficient, a cheaper method of recycling the acid is needed. Without recycling, the acid must be neutralized and properly disposed of before the sugar can be fully utilized. Low strong acid concentrations can be used in place of strong acids; however, this requires much higher temperatures to achieve decent yields and results in byproducts that are poisonous to yeast and bacteria (Badger 2002; Taherzadeh and Karimi, 2007). Similarly, the use of environmentally friendly acids that obtain similar hydrolysis rates to that of the caustic acids are of particular interest.

SUMMARY

In one aspect, the present disclosure provides methods of hydrolysis of polysaccharides and cellulosics by using a mixture of an amino acid with an acid or amino acids salts without an acid. In one aspect, the present disclosure provides a method of hydrolyzing a polysaccharide to obtain one or more monosaccharides comprising:

(a) admixing the polysaccharide with a hydrolysis solution to form a slurry, wherein the hydrolysis solution comprises either a mixture of an amino acid and an acid or an acid salt of an amino acid with or without an acid in a solvent; and (b) heating the slurry to hydrolyze the polysaccharide to one or more monosaccharides.

In some embodiments, the polysaccharide is obtained from a polysaccharide source selected from a plant, an algae, a plant by-product, crystalline cellulose, waste stream cellulose, and a feed stock cellulose. In some embodiments, the plant is switch grass. In other embodiments, the plant is cotton. In other embodiments, the plant is miscanthus. In some embodiments, the algae is seaweed. In some embodiments, the plant by-product is straw, wood, wood pulp, paper board, corn stover, sorghum stover, saw dust, waste of cotton plants, waste of sugar cane plants, orange peel waste, or paper. In some embodiments, the polysaccharide source comprises one or more polysaccharides. In some embodiments, the polysaccharide is cellulose. In other embodiments, the polysaccharide is hemicellulose. In other embodiments, the polysaccharide is pectin.

In some embodiments, the monosaccharide is glucose. In some embodiments, the monosaccharide is D-glucose. In other embodiments, the monosaccharide is L-glucose. In other embodiments, the monosaccharide is xylose. In other embodiments, the monosaccharide is fructose. In some embodiments, the monosaccharide is D-fructose. In some embodiments, the monosaccharide is L-fructose. In some embodiments, the monosaccharide is a mixture of any of these monosaccharides.

In some embodiments, the hydrolysis solution comprises an amino acid with an acid in a solvent. In some embodiments, the amino acid is a canonical amino acid. In some embodiments, the amino acid is glycine. In some embodiments, the acid is an acid with a $pK_a$ of less than 3.0. In some embodiments, the acid is nitric acid, sulfuric acid, phosphoric acid, carboxylic acid$_{(C \leq 12)}$, substituted carboxylic acid$_{(C \leq 12)}$, hydrobromic acid, hydrochloric acid, hydroiodic acid, hydrogen bromide, hydrogen chloride, hydrogen iodide, or a mixture thereof. In some embodiments, the acid is an inorganic acid selected from: nitric acid, sulfuric acid, phosphoric acid, hydrobromic acid, hydrochloric acid, hydroiodic acid, hydrogen bromide, hydrogen chloride, hydrogen iodide, or a mixture thereof. In some embodiments, the acid is hydrogen chloride or hydrochloric acid. In other embodiments, the hydrolysis solution comprises an acid salt of an amino acid with or without an acid in a solvent. In some embodiments, the hydrolysis solution comprises an acid salt of a canonical amino acid in a solvent. In some embodiments, the acid salt is a salt of an inorganic acid. In some embodiments, the acid salt is hydrochloric acid salt. In some embodiments, the amino acid is glycine. In other embodiments, the hydrolysis solution is Oil Safe AR®. In some embodiments, the hydrolysis solution is 200% concentration of the starting concentration of Oil Safe AR®. In some embodiments, the hydrolysis solution is a mixture of hydrochloric acid and glycine. In some embodiments, the hydrolysis solution comprises a mixture of hydrochloric acid and glycine with a ratio of hydrochloric acid to glycine from about 1:10 to about 10:1 as a mole ratio. In some embodiments, the ratio of hydrochloric acid to glycine is from about 1:5 to about 5:1 as a mole ratio. In some embodiments, the ratio of hydrochloric acid to glycine is about 1:1 as a mole ratio. In some embodiments, the ratio of hydrochloric acid to glycine is about 2:3 as a mole ratio. In some embodiments, the ratio of hydrochloric acid to glycine is about 1:4 as a mole ratio.

In some embodiments, the slurry comprises a concentration of hydrolysis solution from about 1 wt % to about 95 wt % of solids. In some embodiments, the concentration of hydrolysis solution is from about 1 wt % to about 50 wt % of solids. In some embodiments, the concentration of hydrolysis solution is from about 5 wt % to about 35 wt % of solids. In some embodiments, the method comprises heating the slurry to a temperature from about 25° C. to about 150° C. In some embodiments, the temperature is from about 50° C. to about 150° C. In some embodiments, the temperature is from about 50° C. to about 100° C. In some embodiments, the method comprises heating the slurry for a time period from about 5 minutes to about 3 days. In some embodiments, the time period is from about 10 minutes to about 360 minutes. In some embodiments, the method comprises pressurizing the slurry to a pressure from about 10 psi to about 150 psi. In some embodiments, the pressure is from about 10 psi to about 30 psi. In some embodiments, the solvent is water.

In some embodiments, the method produces a food grade monosaccharide. In some embodiments, the monosaccharide is formulated as an additive for animal feed. In other embodiments, the monosaccharide is formulated as an additive for human food. In some embodiments, the monosaccharide further comprises the amino acid or the acid salt of the amino acid. In some embodiments, the method further comprises separating the hydrolyzed monosaccharide from the slurry before using the monosaccharide. In some embodiments, the method further comprises purifying the monosaccharide. In some embodiments, the method further comprises separating the amino acid from the slurry. In some embodiments, the method produces a product mixture comprising the food grade monosaccharide, the amino acid or an acid salt of the amino acid, and the acid. In some embodiments, the pH of the product mixture is adjusted before use. In other embodiments, the pH of the product mixture is not adjusted before use. In some embodiments, the amino acid is glycine. In some embodiments, the acid is hydrochloric acid. In some embodiments, the monosaccharide is glucose. In other embodiments, the monosaccharide is xylose. In other embodiments, the monosaccharide is fructose.

In another aspect, the present disclosure provides methods of preparing biodiesel or a bio-alcohol comprising:
(A) obtaining a monosaccharide prepared according to any one of claims 1-64; and either
(B') incubating the monosaccharide with a yeast under conditions suitable to produce a bio-alcohol; or
(B") incubating the monosaccharide with a micro algae under conditions suitable to produce a biodiesel,
whereby bioalcohol or biodiesel is produced. In some embodiments, the monosaccharide is glucose, xylose, fructose, or a mixture thereof. In some embodiments, the biodiesel comprises a triglyceride. In some embodiments, the bio-alcohol is ethanol.

In yet another aspect, the present disclosure provides preservative compositions comprising:
(A) water,
(B) either a mixture of an amino acid and an acid or an acid salt of an amino acid with or without an acid; and
(C) citric acid.

In some embodiments, the composition comprises a mixture of an amino acid and an acid such as a mixture of glycine and hydrochloric acid. In other embodiments, the composition comprises an acid salt of an amino acid such as glycine hydrochloride. In some embodiments, the composition comprises from about 50 wt. % to about 99 wt. % water or comprises from about 85 wt. % to about 97.5 wt. % water. In some embodiments, the composition comprises 95 wt. % water. In some embodiments, the composition comprises from 1 wt. % to 20 wt. % of the mixture of an amino acid and an acid or an acid salt of an amino acid or from 2.5 wt. % to 7.5 wt. % of the mixture of an amino acid and an acid or an acid salt of an amino acid. In some embodiments, the composition comprises about 5 wt. % of the mixture of an amino acid and an acid or an acid salt of an amino acid. In some embodiments, the composition comprises from 1 wt. % to 10 wt. % citric acid or comprises from 2.5 wt. % to 7.5 wt. % citric acid. In some embodiments, the composition comprises 5 wt. % citric acid.

In some embodiments, the composition has a pH from −1 to 6.5 or a pH from −0.5 to 4. In some embodiments, the composition has a pH of about 2. In some embodiments, the composition is used to preserve animal feed such as hay or plant or grain sprouts. In some embodiments, the plant or gran sprouts are alfalfa sprouts or wheat sprouts. In some embodiments, the composition consists essentially of water, the mixture of an amino acid and an acid or an acid salt of an amino acid, and citric acid. In some embodiments, the composition consists of water, the mixture of an amino acid and an acid or an acid salt of an amino acid, and citric acid.

In still yet another aspects, the present disclosure provides methods of preserving an animal feed comprising treating the animal feed with a preservative composition described herein for a time period from about 1 hour to about 2 weeks. In some embodiments, the animal feed is hay. In some embodiments, the animal feed is alfalfa sprouts or wheat sprouts. In some embodiments, the method comprises treating the organic matter with the preservative composition in a ratio from 1:1 to 1000:1. In some embodiments, the ratio is from 5:1 to 100:1. In some embodiments, the ratio is about 10:1. In some embodiments, the preservative composition comprises glycine hydrochloride. In some embodiments, the time period is from about 12 hours to about 1 week. In some embodiments, the time period is from about 24 hours to about 5 days. In some embodiments, the time period is about 4 days. In some embodiments, the methods result in no distinguishable aroma after treatment.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE DISCLOSURE

Figure 1:
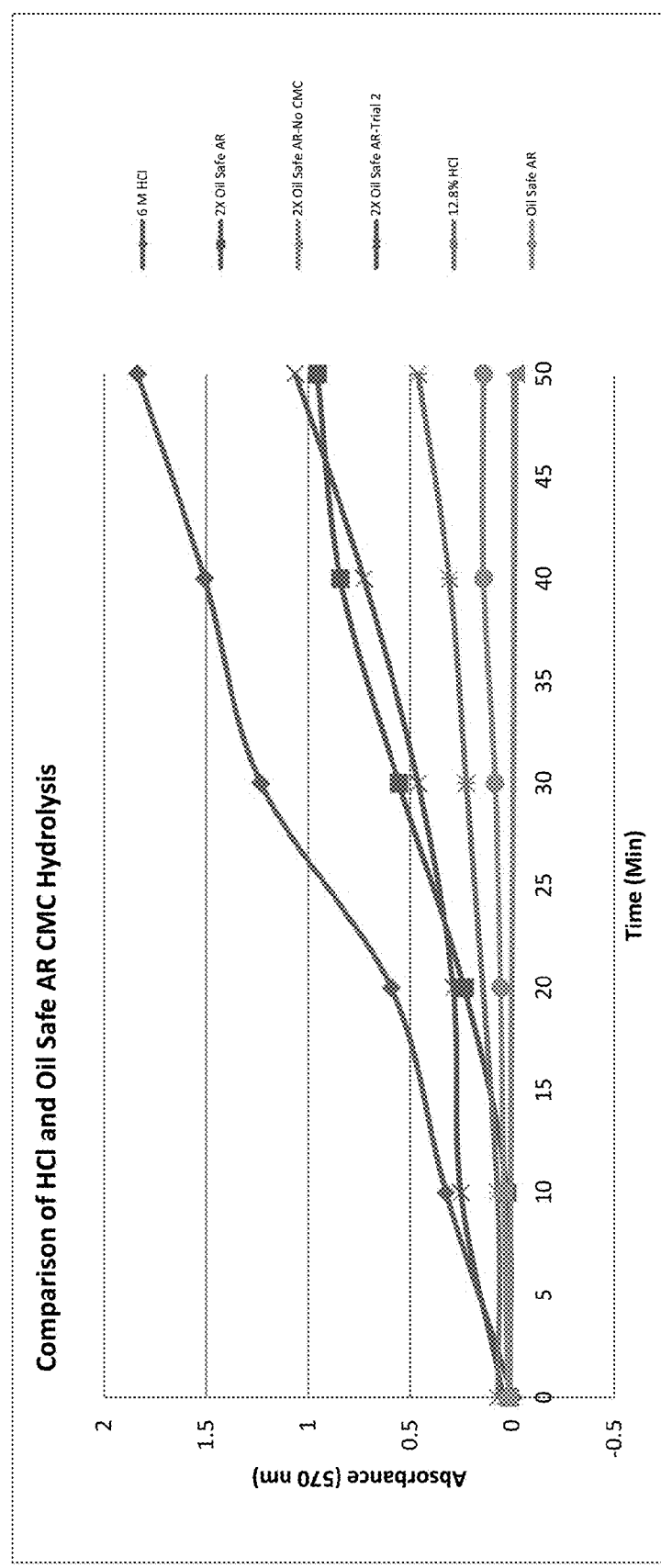
FIG. 1 shows a comparison of Oil Safe AR® at original and 2× concentrations to both 19% and 12.8% HCl solutions in its ability to hydrolyze carboxymethylcellulose (CMC). The results show that 2× Oil Safe AR yielded a sugar concentration in between the HCl solutions.

In some embodiments, the present disclosure relates to using an environmentally friendly acid to hydrolyze a polysaccharide into its component monosaccharides. In some embodiments, the method relates to using the environmentally friendly acid which does not require the use of high temperatures, high pressures, or high concentrations of strong acids. In some embodiments, the monosaccharides produced by the hydrolysis may be used in a feed or a nutritional supplement for animals or humans as well as in the production of a biofuel.

I. POLYSACCHARIDES

In some aspects of the present disclosure, a wide variety of different polysaccharides are hydrolyzed using an amino acid solution. In some embodiments, the amino acid solution is prepared by mixing one or more amino acids with an inorganic acid. The polysaccharides that may be used in the hydrolysis methods described herein include cellulose, cellulose derivatives, carboxymethylcellulose, hemicellulose, amylose, pectin, or chitin. Within the context of this application, polysaccharide encompasses all cellulosic materials. Polysaccharides are long polymers of individual sugar molecules joined by one or more glycosidic bonds and may be either linear or branch. Some polysaccharides that may be used include at least one or more glucose, xylose, or fructose molecules. In some embodiments, the polysaccharide further comprises one or more additional compounds such as lignin. Furthermore, it is contemplated that the polysaccharide that may be used includes a mixture of different polysaccharide molecules.

Additionally, in some embodiments, the polysaccharide is obtained from a wide variety of sources. Some non-limiting examples of polysaccharide sources include corn stover, sugarcane wase, miscanthus, sorghum stover, potato peels, cotton, seaweed, switch grass, wood, or straw. The polysaccharide may be obtained from a plant, an algae, a plant by-product, crystalline cellulose, a waste stream cellulose, and a feed stock cellulose. Some examples of plants from which cellulose can be obtained include, but are not limited to, switch glass, cotton, or miscanthus. Some non-limiting examples of algae from which the polysaccharide may be obtained include seaweed including, but not limited to, red seaweed, green seaweed, and brown seaweed. Some non-limiting examples of plant or algae by-products include straw, wood, wood pulp, paper board, corn stover, sorghum stover, saw dust, waste of cotton plants, waste of sugar cane plants, orange peel waste, or paper such as newspaper. In some particular embodiments, the polysaccharide is originally obtained from an algae, a plant, or a by-product of either of these groups. In some embodiments, the algae or plant by-product is any material derived from or obtained directly from the algae or plant.

II. AMINO ACIDS AND METHODS OF HYDROLYSIS

In some aspects, the present disclosure provides methods of using an amino acid with an acid or an acid salt of an amino acid to obtain a monosaccharide from a polysaccharide such as cellulose. In some embodiments, the amino acid is any compound which contains both an amine group and a carboxylic acid connected by one or more aliphatic groups. In particular, the amino and carboxylic groups are attached to the same aliphatic carbon (known as the α carbon) wherein the α carbon may be further substituted with any group such as an alkyl group, an aryl group, a heterocycloalkyl group, a heteroaryl group, or a substituted version of any of these groups. The amino acids, in some embodiments of the present disclosures, are selected from the 20 canonical amino acids or naturally occurring derivatives thereof. In some embodiments, the amino acid is selected from: glycine, alanine, leucine, isoleucine, valine, proline, phenylalanine, tyrosine, tryptophan, serine, threonine, lysine, histidine, arginine, cysteine, methionine, glutamic acid, aspartic acid, glutamate, or aspartate.

In some aspects, the amino acid is mixed with an acid to form a hydrolysis solution. In some embodiments, the acid has a $pK_a$ of less than 3.0. In some embodiments, the $pK_a$ is less than 0.0. In some embodiments, the acid is an inorganic acid, carboxylic acid$_{(C \leq 12)}$ or a substituted carboxylic acid$_{(C \leq 12)}$. Some non-limiting examples of a carboxylic acid$_{(C \leq 12)}$ or a substituted carboxylic acid$_{(C \leq 12)}$ include acetic acid, trifluoroacetic acid, or trichloroacetic acid. In some embodiments, the inorganic acid is selected from: nitric acid, sulfuric acid, phosphoric acid, hydrobromic acid, hydrochloric acid, hydroiodic acid, hydrogen bromide, hydrogen chloride, or hydrogen iodide, or a mixture thereof. In some embodiments, the inorganic acid is hydrochloric acid or hydrogen chloride.

The amino acids of the present disclosure may be used as the acid salt form of the amino acids. In some embodiments, the acid salt is a salt obtained from reacting the amino acid with a strong acid. The acids that may be used to form the acid salt of the amino acid are selected from nitric acid, sulfuric acid, phosphoric acid, acetic acid, hydrobromic acid, hydrochloric acid, hydroiodic acid, hydrogen bromide, hydrogen chloride, hydrogen iodide, or a mixture thereof. In one embodiments, the acid used is hydrogen chloride or hydrochloric acid.

The acid salt is produced by adding the amino acid to a solution and then admixing an acid with the solution. As would be obvious to a person of skill in the art, the acid salt could also be produced by adding the acid to the solution and then adding the amino acid to the solution containing the acid. A wide variety of solvents may be used to obtain the desired acid salt of amino acid including water, alcohol$_{(C \leq 12)}$, or a substituted alcohol$_{(C \leq 12)}$. In some embodiments, this solution can be used as produced to hydrolyze the polysaccharide. The solution containing the amino acid with the inorganic acid or the acid salt of the amino acid may be called a "hydrolysis solution."

In some aspects of the present disclosure, the polysaccharide is hydrolyzed using the acid salt of an amino acid or a mixture of an amino acid with an acid in a solvent. In some embodiments, the hydrolysis comprises using one or more amino acids mixed with an acid. In some embodiments, the hydrolysis is preformed under increased pressure. The increased pressure that may be used to hydrolyze the polysaccharide is from about 10 psi to about 150 psi. In some aspects, the pressure is from about 1 to about 3 times atmospheric pressure or about 10 psi to about 30 psi. Additionally, the hydrolysis reaction is performed for a time period from about 1 minute to about 24 hours. In some embodiments, the time period is about 5 minutes to about 720 hours. In some embodiments, the time period is about 10 minutes to about 360 minutes. The hydrolysis time period that may be used is from about 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 125 minutes, 150 minutes, 175 minutes, 200 minutes, 225 minutes, 250 minutes, 275 minutes, 300 minutes, 325 minutes, 350 minutes, 355 minutes, 360 minutes, 365 minutes, 370 minutes, 375 minutes, or any range derivable therein. Additionally, in some embodiments, the hydrolysis reaction further comprises heating to a temperature from about room temperature to about 150° C. In some embodiments, the temperature is from about 50° C. to about 150° C. In some embodiments, the temperature is from about 50° C. to about 100° C. The temperature that may be used is from about 25, 30, 35, 40, 45, 50, 55, 60, 65, 70, 75, 80, 85, 90, 95, 100, 105, 110, 115, 120, 125, 130, 135, 140, 145, 150° C. or any range derivable thereof.

III. ANIMAL FEED, NUTRITIONAL SUPPLEMENT, OR BIOFUEL

In some aspects, the present disclosure provides methods of using the monosaccharides obtained in a variety of different products or methods. One of the methods in which the monosaccharides obtained herein can be used is in the production of an animal feed. The monosaccharide may be used to supplement another type of feed to increase the amount of the monosaccharide or may be given to the animal alone as a food source. In some embodiments, the monosaccharide is given to an animal selected from: a cow, horse, chicken, pig, duck, goose, turkey, or other livestock animal and a cat, dog, bird, guinea pig, turtle, fish, or other companion animal.

In another aspect, the present disclosure provides methods of using the monosaccharide to provide food to a human. The monosaccharide may be added to other food, used as a nutritional supplement to increase the nutrient value of the food, or given directly to the human. Without wishing to be bound by any theory, the monosaccharides obtained are further purified before they are used as a food source. The monosaccharide may be prepared as a powder, a tablet or capsule, or a solution. In some embodiments, the hydrolysis solution and the obtained monosaccharides are used directly without further purification as an animal feed or for human consumption. The monosaccharide may be prepared as a powder, a tablet or capsule, or a solution.

In still another aspect, the present disclosure provides monosaccharides which are useful for providing to a yeast, bacteria, micro-algae, or other micro-organism to obtain a biofuel. The yeast, bacteria, micro-algae, or other microorganism converts the monosaccharide used into a substance which is convertible into energy. The substances that may be used include, but are not limited to, a bio-diesel or a bio-alcohol. In some embodiments, the bio-diesel is a hydrocarbon mixture including one or triacylglycerides or other fatty acid analogs. In some embodiments, the bio-alcohol is an alcohol$_{(C \leq 12)}$. In some embodiments, the alcohol$_{(C \leq 12)}$ is ethanol. The use of monosaccharide to obtain a biofuel is described in U.S. Pat. No. 8,211,689, US Patent Publication 2012/0156717, PCT WO 2013/017289, Taherzadeh and Karimi (2007), Badger (2002), Wright and Power (1987), Farina, et al., (1988), Cuzens and Miller (1997), and Pauly and Keegstra (2008), each of which are incorporated herein by reference.

IV. PRESERVATIVE COMPOSITIONS

In some aspects, the present compositions may be used to show the decomposition of hay or plant sprouts. In some embodiments, the preservative composition is used on hay. In other embodiments, the preservative composition is used on plant sprouts. Some non-limiting examples of plant based materials which may be used include animal feed such as hay, plant sprouts such as bean sprouts, alfalfa sprouts, or wheat sprouts, or other plant based feed stocks. In some aspects, these preservative composition or solution comprise water, a C1-C12 carboxylic acid or substituted carboxylic acid, and an acid salt of an amino acid or an amino acid and another acid. In some embodiments, the carboxylic acid is a polycarboxylic acid (e.g. contains two or more —$CO_2H$ groups) such as succinic acid, citric acid, or maleic acid.

In some embodiments, the compositions comprises at least 50% water. In some embodiments, the composition comprises from 50% to 99% water, from 80% to 97.5% water, or from 85% to 95% water. In some embodiments, the amount of water in the composition is from about 50%, 55%, 60%, 65%, 70%, 75%, 80%, 82%, 84%, 86%, 88%, 90%, 92%, 94%, 96%, 98%, 99%, to about 99.5%, or any range derivable therein. In some embodiments, the water is distilled water, deionized water, or millipure water.

In some embodiments, the composition comprises from about 1% to about 20% of the carboxylic acid. In some embodiments, the composition comprises from 1% to 10% of the carboxylic acid, from 2.5% to 7.5% of the carboxylic acid, to 4% to about 6% of the carboxylic acid. In some embodiments, the amount of carboxylic acid in the composition is from about 1%, 2%, 2.5%, 3%, 3.5%, 4%, 4.5%, 5%, 5.5%, 6%, 6.5%, 7%, 8%, 9%, 10%, 12%, 14%, 16%, 18%, to about 20%, or any range derivable therein. In some embodiments, the carboxylic acid is C1-C12 tricarboxylic acid such as citric acid.

In some embodiments, the composition comprises from about 1% to about 20% of the amino acid or the salt of the amino acid. In some embodiments, the composition comprises from 1% to 10% of the amino acid or the salt of the amino acid, from 2.5% to 7.5% of the amino acid or the salt of the amino acid, to 4% to about 6% of the amino acid or the salt of the amino acid. In some embodiments, the amount of the amino acid or the salt of the amino acid in the composition is from about 1%, 2%, 2.5%, 3%, 3.5%, 4%, 4.5%, 5%, 5.5%, 6%, 6.5%, 7%, 8%, 9%, 10%, 12%, 14%, 16%, 18%, to about 20%, or any range derivable therein. In some embodiments, the amino acid and an acid is a canonical amino acid such as glycine, valine, leucine, or isoleucine. In some embodiments, the acid is an inorganic acid such as hydrochloric acid or hydrogen chloride. In some embodiments, the composition comprises an acid salt of an amino acid. In some embodiments, the acid salt of an amino acid is a hydrogen chloride salt of a canonical amino acid such as glycine hydrochloride or valine hydrochloride.

The composition may be used in a diluted form. In some embodiments, the preservation composition is diluted with water. In some embodiments, the preservation composition is diluted from 2:1 water to preservation composition to about 1000:1 water to preservation composition. In some embodiments, the organic matter may be treated with the preservation composition or a diluted version thereof. The composition may be used by coating, submerging, or soaking the organic matter with the composition or a diluted version thereof. In some embodiments, the organic matter may be left in the preservation solution or diluted version thereof for hours, days, weeks, or months. The preservation compositions may be used to prevent degradation of the organic matter or to reduce or eliminate microbial growth.

V. DEFINITIONS

An "amino acid" is a functional group which contains a carboxylic acid (—$CO_2H$) and an amine (—$NH_2$) group on the same carbon aliphatic skeleton which may contain other functional groups attached to the aliphatic skeleton. In some embodiments, the aliphatic group is a saturated aliphatic group. In some embodiments, the term "amino acids" refer to a functional group in which both the —$CO_2H$ and the —$NH_2$ are attached to the same carbon atom; which may also be known as an "α-amino acid". In some embodiments, the aliphatic group is substituted with one or more alkyl$_{(C≤12)}$, aryl$_{(C≤12)}$, heteroaryl$_{(C≤12)}$, or a substituted version of these groups. In its preferred embodiment, the term "amino acid" refers to one of the naturally occurring or commercially available amino acids as well as their enantiomers and diastereomers. In its most preferred embodiment, the term "amino acids" refers the 20 canonical amino acids, a protected version of one of the 20 canonical amino acids, and their enantiomers and diastereomers. As used herein, the term "amino acid" can also refer to salt of the amino acid unless otherwise specified.

As used herein, the term "about" refers to the stated value, plus or minus 5% of that stated value.

For the groups and classes below, the number of carbon atoms in the group is as indicated as follows: "$C_n$" defines the exact number (n) of carbon atoms in the group/class. "$C≤n$" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "$C_{n-n'}$" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —$CH_3$ (Me), —$CH_2CH_3$ (Et), —$CH_2CH_2CH_3$ (n-Pr or propyl), —$CH(CH_3)_2$ (i-Pr, $^i$Pr or isopropyl), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tert-butyl, t-butyl, t-Bu or $^t$Bu), and —$CH_2C(CH_3)_3$ (neo-pentyl) are non-limiting examples of alkyl groups. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$SCH_3$, —$OCH_3$, —$OCH_2CH_3$, —C(O)$CH_3$, —$NHCH_3$, —$NHCH_2CH_3$, —NHC(NH)$NH_2$, —N($CH_3$)$_2$, —C(O)$NH_2$, —OC(O)$CH_3$, or —S(O)$_2NH_2$. The following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —$C_6H_4CH_2CH_3$ (ethylphenyl), naphthyl, and a monovalent group derived from biphenyl. When this term is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$SCH_3$, —$OCH_3$, —$OCH_2CH_3$, —$C(O)CH_3$, —$NHCH_3$, —$NHCH_2CH_3$, —$NHC(NH)NH_2$, —$N(CH_3)_2$, —$C(O)NH_2$, —$OC(O)CH_3$, or —$S(O)_2NH_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. When this term is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$SCH_3$, —$OCH_3$, —$OCH_2CH_3$, —$C(O)CH_3$, —$NHCH_3$, —$NHCH_2CH_3$, —$NHC(NH)NH_2$, —$N(CH_3)_2$, —$C(O)NH_2$, —$OC(O)CH_3$, or —$S(O)_2NH_2$.

The term "alkoxy" when used without the "substituted" modifier refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —$OCH(CH_3)_2$ (isopropoxy), —$OC(CH_3)_3$ (tert-butoxy), —$OCH(CH_2)_2$, —O-cyclopentyl, and —O-cyclohexyl. The term "alcohol" corresponds to an alkane, as defined above, wherein at least one of the hydrogen atoms has been replaced with a hydroxy group. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$SCH_3$, —$OCH_3$, —$OCH_2CH_3$, —$C(O)CH_3$, —$NHCH_3$, —$NHCH_2CH_3$, —$NHC(NH)NH_2$, —$N(CH_3)_2$, —$C(O)NH_2$, —$OC(O)CH_3$, or —$S(O)_2NH_2$.

The term "carboxylic acid" when used without the "substituted" modifier refers to a compound of the formula, $RCO_2H$, in which R is a hydrogen atom, an alkyl group, or an aryl group, as those terms are defined above. Non-limiting examples include: $HCO_2H$, $H_3CCO_2H$, or $H_3C(CH_2)_2CO_2H$. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$SCH_3$, —$OCH_3$, —$OCH_2CH_3$, —$C(O)CH_3$, —$NHCH_3$, —$NHCH_2CH_3$, —$NHC(NH)NH_2$, —$N(CH_3)_2$, —$C(O)NH_2$, —$OC(O)CH_3$, or —$S(O)_2NH_2$.

The term "organic matter" refers to any carbon based material which provides energy or may be used as a feedstock for humans or other animals. "Biomass" is a subset of organic matter which refers to a carbon based material derived from living or recently living organisms. "Animal feedstock" is a material which may be feed to livestock or other animals to provide nutrition to the animal. Some non-limiting examples of an animal feedstock include plant based materials such as corn, wheat, or sorghum, and plant material such as hay or silage.

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

V. EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Hydrogen Glycine Preparation. 55 grams of glycine (0.72 moles) were added to a flask and filled to 60 mL with deionized water. The mixture was then stirred and heated until the glycine was completely dissolved. Once dissolved, 60 mL of 38% hydrochloric acid (0.72 moles) was slowly added. The solution was then allowed to cool to room temperature.

Oil Safe AR®. The Oil Safe AR® acid was purchased from The Heartland Energy Group. This acid was either directly used in hydrolyzing cellulose or concentrated to 2× the original solution by evaporation at 60° C.

Dinitrosalicyclic Acid Sugar Assay. The DNS sugar assay utilizes the reduction of dinitrosalicyclic acid by simple monosaccharides to create a change in color, respective the concentration of sugar in each sample (Rivers). A 1% dinitrosalicyclic acid solution was created with 0.25 M NaOH and 0.2% phenol. Another solution of 40% Sodium Potassium Tartrate was made to act as a color stabilizer to be added to the sample after the reaction. This procedure requires the experimental sample to be mixed with the DNS Assay solution and heated at approximately 100° C. for ten minutes. After the colorimetric reaction has occurred, the sodium potassium tartrate solution is added to stabilize the color change. The resulting color change can be measured using the wavelength of 570 nm.

Cellulose Hydrolysis. 5 mL of each acid was added to a glass container. Then, 0.1 grams of carboxymethylcellulose was slowly poured in to each sample. The containers were then capped and placed in a 60° C. incubator. At specific time intervals, 0.4 mL were taken and neutralized by 0.6 mL of a strong KOH solution to a pH above 10 in 1.5 mL microfuge tubes. Then 0.2 mL of the DNS Assay solution was added to each sample, which were then placed in a boiling water bath for ten minutes. At ten minutes, when the color change was stable, the samples were removed and 0.4 mL of the 40% sodium potassium tartrate solution was added. The absorbance of the samples were then measured at 570 nm in a UV-Vis spectrophotometer and compared to a standard curve.

Seaweed Hydrolysis. 5 mL samples of a 6 M hydrochloric acid solution, and a 6 M glycine hydrochloride solution were prepared. The samples were heated to 60° C. Approximately 0.1 grams of seaweed was measured and added to each sample. The acid/seaweed mixtures were placed in an incubator set at 60° C. for one hour. At twenty minute intervals, 0.4 mL were taken from the samples and neutralized to a high pH (>10) with 0.6 mL of a concentrated aqueous NaOH solution.

Switch Grass Hydrolysis. 5 mL samples of water, a 6 M hydrochloric acid solution, and a 6 M glycine hydrochloride solution were prepared. The samples were heated to 60° C. Approximately 0.1 grams of switch grass was measured and added to each sample. The acid/switch grass mixtures were placed in an incubator set at 60° C. for one hour. At 0, 10, 20, 40, and 60 minutes, 0.4 mL were taken from the samples and neutralized to a high pH (>10) with 0.6 mL of a concentrated aqueous NaOH solution.

Seaweed DNS Assay. To each of the neutralized mixtures, 0.2 mL of DNS solution (1% dinitrosalicyclic acid, 0.02% phenol, 0.25 M NaOH) was added. These samples were then placed in boiling water for approximately ten minutes until the brown color remained stable. The samples were then removed and 0.4 mL of a 40% potassium sodium tartrate solution was added to stabilize the color. The solutions were allowed to cool to room temperature and then the absorbance was recorded at 570 nm.

Switch Grass DNS Assay. To each of the neutralized mixtures, 0.2 mL of DNS solution (1% dinitrosalicyclic acid, 0.02% phenol, 0.25 M NaOH) was added. These samples were then placed in boiling water for approximately ten minutes until the brown color remained stable. Then 0.2 mL of each sample was mixed with 0.2 mL of a 40% potassium sodium tartrate solution and 1 mL of deionized water. The solutions were allowed to cool to room temperature and then the absorbance was recorded at 570 nm.

Galvanized Steel Corrosion Test. Approximately 0.1 grams of galvanized steel (in the form of standard paper clips) were weighed and placed in to 5 mL solutions of 6 M HCl, 6 M glycine hydrochloride, and varies proportions of both. After twenty four hours, the steel pieces were removed, rinsed with deionized water, wiped, then dried and weighed. The pieces were then placed back in the acid samples for another twenty four hours and the process was repeated. Decomposition was calculated by percent weight in grams lost.

Example 2—Hydrolysis of Cellulose

The Oil Safe AR® purchased was able to hydrolyze cellulose but only at a very slow rate, only yielding an approximate sugar concentration of 0.12% after fifty minutes. When concentrated to 2× its original value, the 2× concentrated Oil Safe AR® drastically improved to a 0.5% sugar solution. Compared to HCl solutions, this value falls between a 19% and 12.8% HCl solution in terms of final yield as can be seen in FIG. 1.

Figure 2:
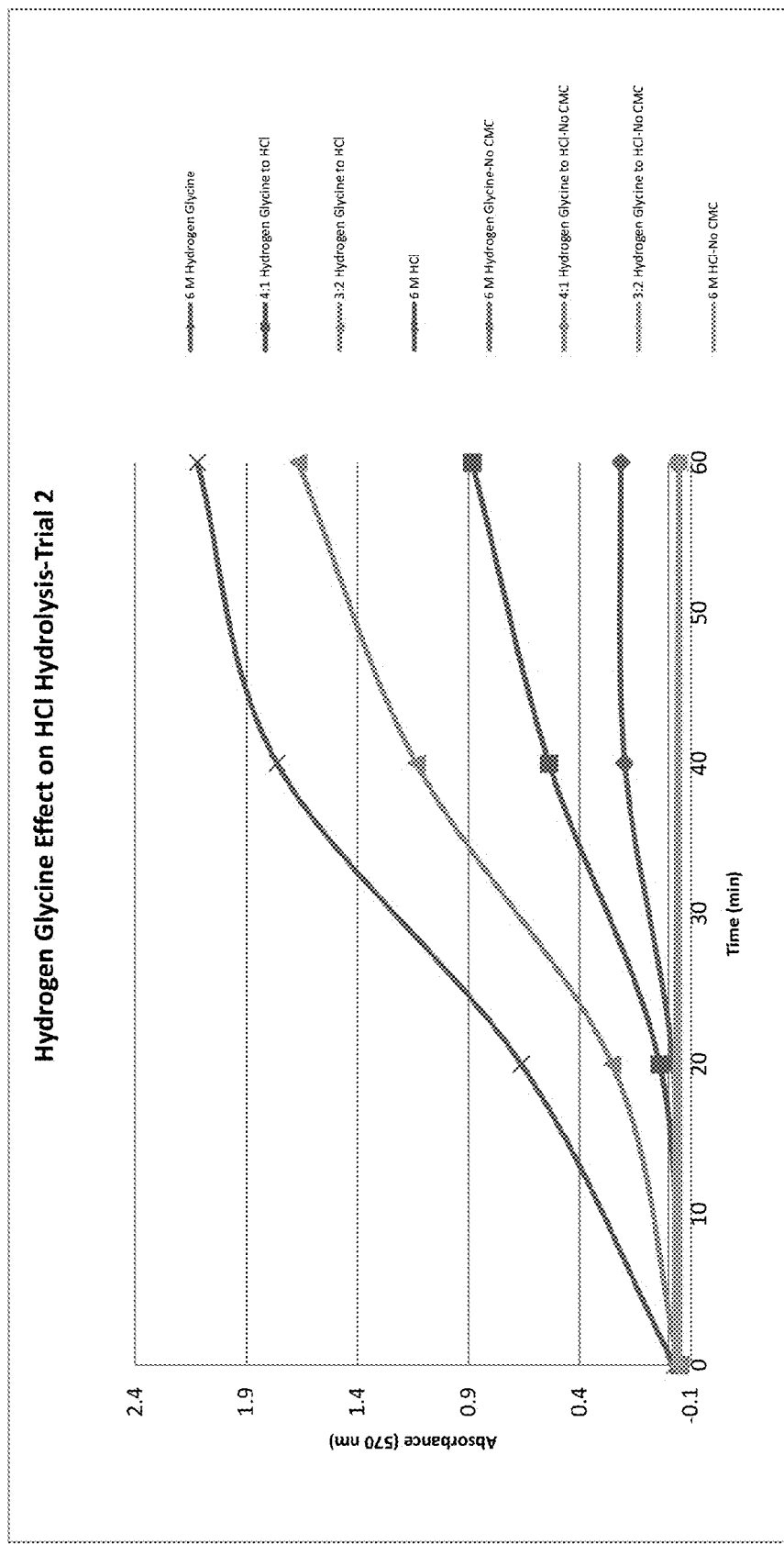
FIG. 2 shows the yield of sugar as a function of time was plotted in relation to the tested acids. Increasing the ratio of HCl to hydrogen glycine results in an increase in the rate of hydrolysis of carboxymethylcellulose.

FIG. 2, on the other hand, depicting the varies combinations of a 6 M hydrogen glycine solution to a 6 M HCl solution shows the general effect of hydrogen glycine on hydrolysis. The additional 6 M HCl solution use with hydrogen glycine increased the rate of the hydrolysis. The 6 M hydrogen glycine solution showed hydrolysis rates equal to that of Oil Safe AR®. Without being bound by any theory, the hydrolyzing effects are described in FIG. 2 are due to hydrogen glycine and how molarity of the solution affects the hydrolysis. As can be seen in FIG. 2, the increased concentration of the hydrogen glycine leads to increased hydrolysis of the cellulose.

Example 3—Hydrolysis of Seaweed and Switch Grass

Figure 3:
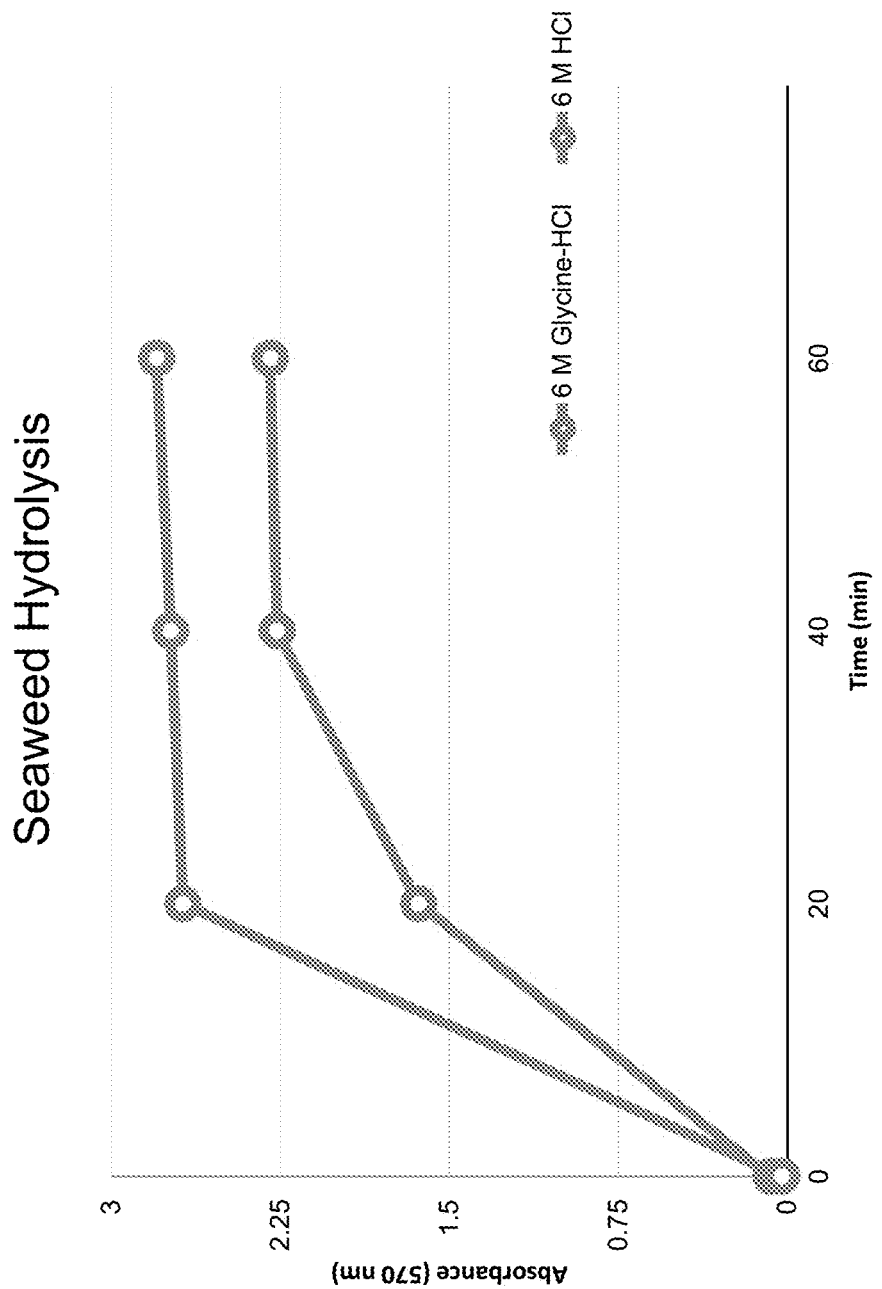
FIG. 3 shows a comparison of the hydrolysis of seaweed by 6M glycine hydrochloride to the hydrolysis of seaweed by a 6M HCl solution measured by the dinitrosalicyclic acid assay.
Figure 4:
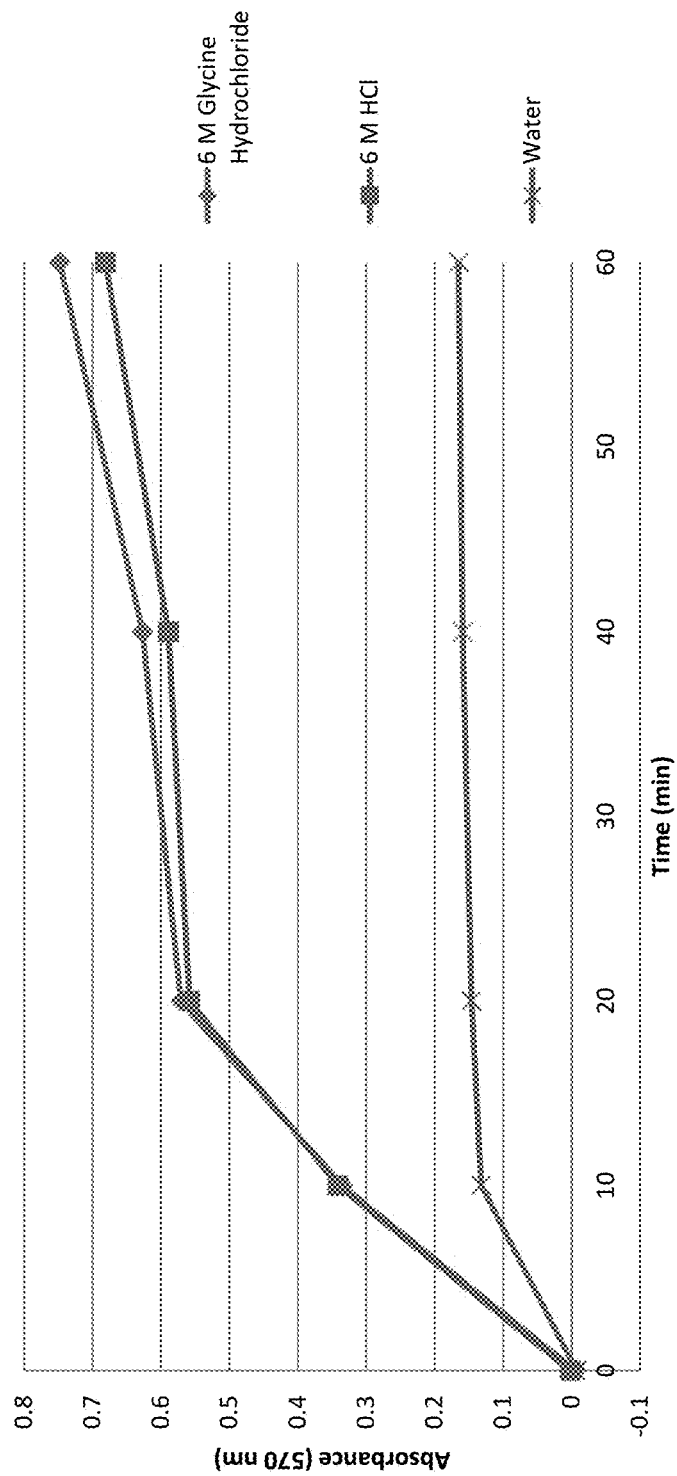
FIG. 4 shows a comparison of the hydrolysis of switchgrass by 6M glycine hydrochloride to the hydrolysis of seaweed by a 6M HCl solution or the hydrolysis of seaweed by water measured by the dinitrosalicyclic acid assay.

Additional experimental data were prepared with seaweed and switch grass to include as additional examples (FIGS. 3 & 4). Both 6M HCl and 6M Glycine HCl performed about the same rate in hydrolyzing either the seaweed or the switch grass. The hydrolysis rates for the switch grass are shown in Table 1.

Example 4—Galvanized Steel Corrosion Test

Corrosion tests were performed using 6M HCl, 6M Glycine HCl and combinations thereof. 6M HCl is the most corrosive (Table 1) with 6M Glycine HCl being the least. The pH was lowered in the case of 6M Glycine HCl but increased in the case of 6M HCl after switch grass hydrolysis (Table 1). In some embodiments of the present disclosure, the 6M Glycine HCl has additional advantage including being non-corrosive and environmentally friendly versus using 6M HCl for the hydrolysis of a polysaccharide, as well as the quality of improving hydrolysis and decreasing corrosion when added to HCl solutions.

TABLE 1

| | Results of Galvanized Steel Corrosion Test via Mass Loss | | | | |
|---|---|---|---|---|---|
| Time (hours) | 6M HCl | 3:2 6M HCl:6M Glycine—HCl | 1:1 6M HCl:6M Glycine—HCl | 2:3 6M HCl:6M Glycine—HCl | 6M Glycine—HCl |
| 0 | 0.1199 | 0.119 | 0.1252 | 0.1243 | 0.1310 |
| 24 | 0.104 | 0.1089 | 0.115 | 0.1193 | 0.1295 |
| 48 | 0.0824 | 0.1008 | 0.1068 | 0.1113 | 0.1261 |
| 72 | 0.0658 | 0.0948 | 0.1008 | 0.103 | 0.1241 |
| Decomposition | 45.1% | 20.3% | 19.5% | 17.1% | 5.3% |

Example 5—Solutions of HCl and Hydrogen Glycine

Figure 5:
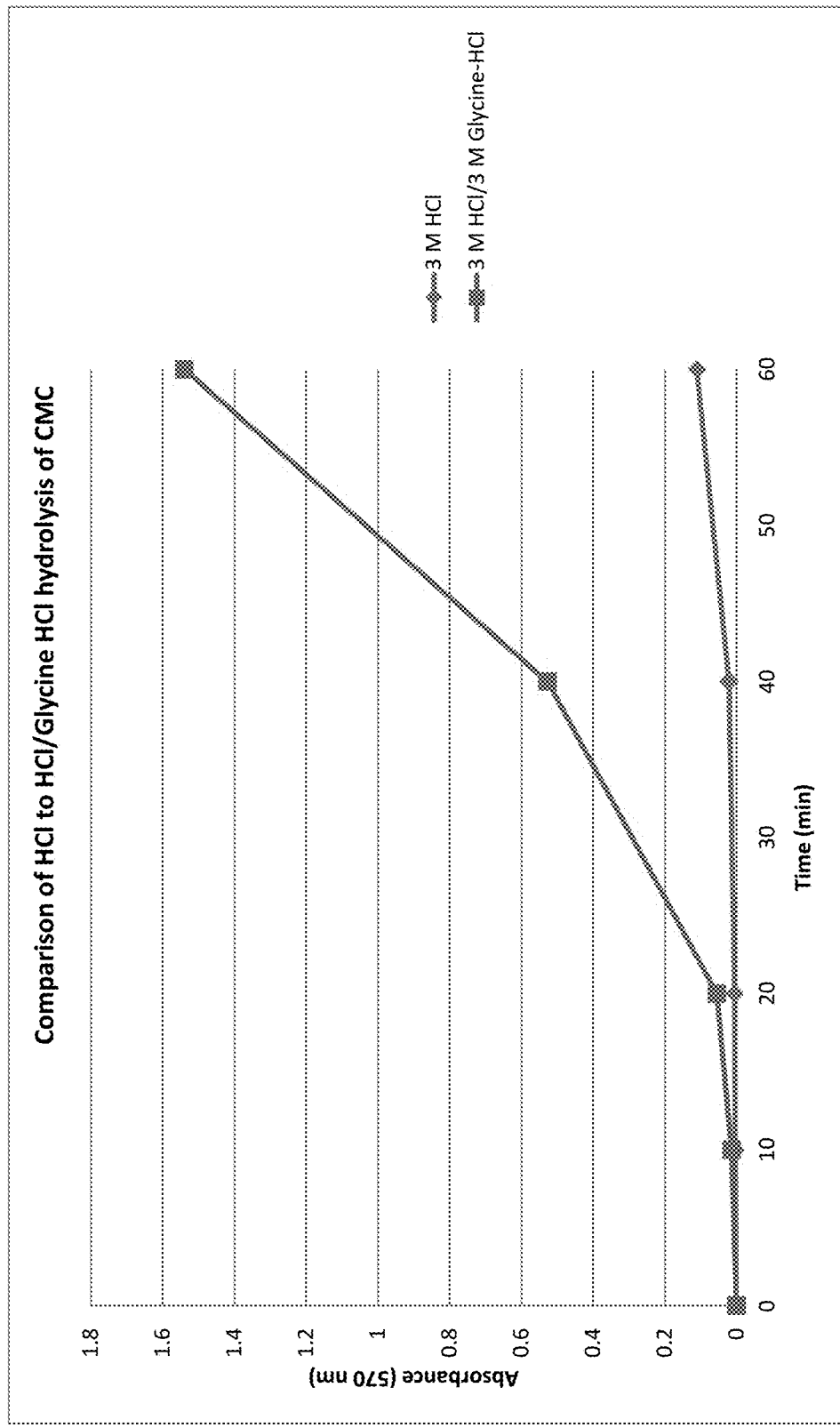
FIG. 5 shows the hydrolysis of carboxymethylcellulose of an HCl/glycine hydrochloride mixture compared to the hydrolysis using only HCl.
Figure 6A:
FIGS. 6A-6F show the treatment of alfalfa (70-80% moisture) at 0 hours in 10% w/w propionic based preservative solution (FIG. 6A), no preservative solution (FIG. 6B), and 10% w/w glycine hydrochloride preservative solution (FIG. 6C). The same alfalfa is shown after 96 hours in the 10% w/w propionic based preservative solution (FIG. 6D), no preservative solution (FIG. 6E), and 10% w/w glycine hydrochloride preservative solution (FIG. 6F).
Figure 6B:
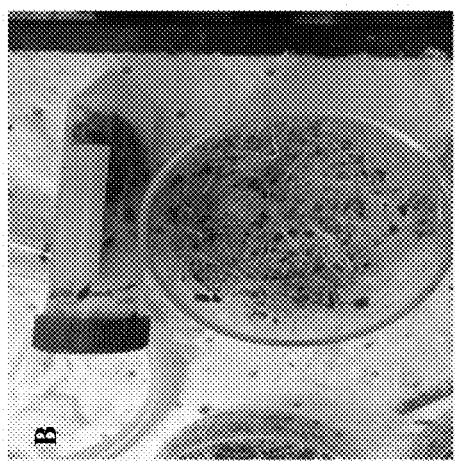
Figure 6C:
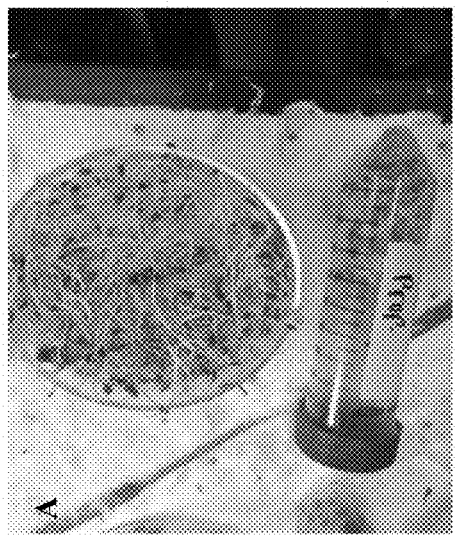
Figure 6D:
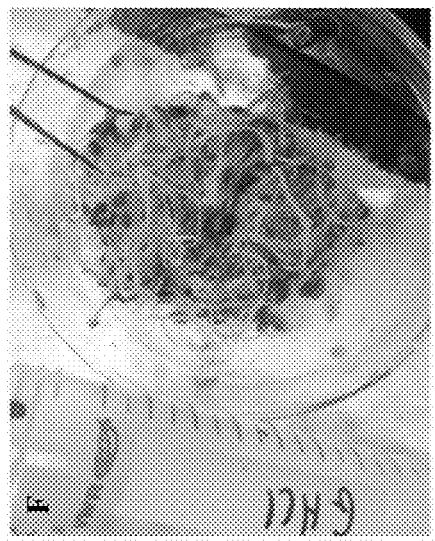
Figure 6E:
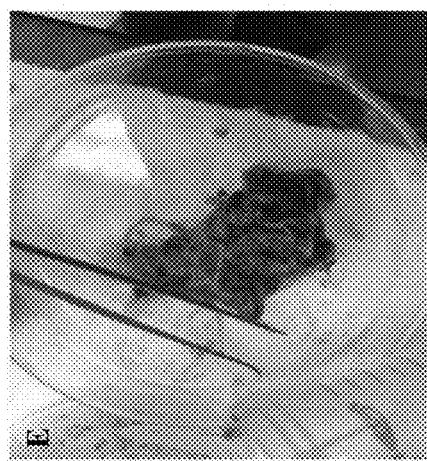
Figure 6F:

As can be seen in FIG. 5, the addition of a hydrogen glycine solution to a solution containing HCl results in significant improve in the hydrolysis over simply using either the HCl or hydrogen glycine solution alone.

Example 6—Preservation of Grass and Biomass Through Treatment of Glycine Preserving Solution A. Methods
1. Alfalfa Preservation Two hay preservatives were tested using fresh alfalfa (moisture content 70-80%) over 96 hours. The preservatives were a 90% water, 5% glycine hydrochloride, 5% citric acid solution (pH~2) and a 65% propionic acid, 30% water and sodium hydroxide, 5% citric acid solution (pH~5.5). 1 gram of each preservative was applied to 10 grams of alfalfa, and was kept in a lightly capped test tube for 96 hours at room temperature. Preservation was judged off of smell, texture, and color retention.

2. Corrosion

Galvanized steel pieces were placed in 1 mL of each preserving solution and allowed to sit for 96 hours. The pieces were then removed, dried, and weighed to determine the total loss in mass.

B. Results

FIGS. 6A-6F shows that the addition of no preservative leads to extreme decomposition and loss of alfalfa. The propionic acid preserving solution had much less decomposition but bleached the alfalfa yellow and left a pungent smell of acid. The glycine hydrochloride preserving solution had near identical preservation as the propionic acid in terms of decomposition while still retaining the color of the alfalfa. The alfalfa did not have any distinguishable aroma from the preservative. As seen from Table 2, the glycine hydrochloride solution also was much less corrosive than a propionic acid solution even with a pH of 2.

TABLE 2

Corrosion of Galvanized Steel in Glycine Hydrocholirde Preservative Solution and a Propionic Acid Preservative Solution

| | Glycine Hydrochloride Solution* | | Propionic Acid Solution** | |
|---|---|---|---|---|
| 0 Hours | 0.0822 g | 0.0790 g | 0.0891 g | 0.0836 g |
| 96 Hours | 0.0810 g | 0.0789 g | 0.0860 g | 0.0807 g |
| Percentage Mass Loss | 1.45% | 0.13% | 3.47% | 3.47% |

*Glycine Hydrochloride Solution (90% water, 5% glycine hydrochloride, 5% citric acid) with a pH of ~2.
**Propionic Acid solution (65% propionic acid, 30% water and sodium hydroxide, 5% citric acid) with a pH of ~4.5.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference:

U.S. Pat. No. 8,211,689
U.S. Pat. No. 8,747,561
U.S. Pat. No. 8,853,446
U.S. Patent Publication 2012/0156717
U.S. Patent Publication 2014/0041690
PCT WO 2013/017289
Badger, "Ethanol from Cellulose: A General Review," Janick and Whipkey (Eds.), ASHS Press, Alexandra, Va., 2002.
Curzens and Miller, "Acid hydrolysis of bagasse for ethanol production," *Renew. Energy*, 10:285-290, 1997.
Farina, et al., "Fuel Alcohol Production from Agricultural Lignocellulosic Feedstocks," *Energy Source Part A*, 10:231-237, 1988.
Pauly and Keegstra, "Cell-wall carbohydrates and their modifications as a resource for biofuels," *The Plant Journal*, 54:559-568, 2008.
Taherzadeh and Karimi, "Acid-based Hydrolysis Processes for Ethanol from Lignocellulosic Materials: A Review," *BioResources*, 2007.
Wright and Powers, "Energy from Biomass and Wastes, Comparative Technical Evaluation of Acid Hydrolysis Processes for Conversion of Cellulose to Alcohol," *Energy Biomass Wastes*, 949-971, 1987.

What is claimed is:

1. A method of hydrolyzing a polysaccharide to obtain one or more monosaccharides comprising:
   (a) admixing the polysaccharide with a hydrolysis solution to form a slurry, wherein the hydrolysis solution comprises a mixture of hydrochloric acid and glycine with a ratio of hydrochloric acid to glycine from about 1:10 to 10:1 as a mole ratio; and
   (b) heating the slurry to hydrolyze the polysaccharide to one or more monosaccharides.

2. The method of claim 1, wherein the polysaccharide is obtained from a polysaccharide source selected from a plant, an algae, a plant by-product, crystalline cellulose, waste stream cellulose, and a feed stock cellulose.

3. The method of claim 1, wherein the monosaccharide is glucose, fructose, xylose, or a mixture thereof.

4. The method of claim 1, wherein the slurry comprises a concentration of hydrolysis solution from about 1 wt % to about 95 wt % of solids.

5. The method of claim 1, wherein the method comprises heating the slurry to a temperature from about 25° C. to about 150° C.

6. A preservative composition comprising:
   (A) water,
   (B) a mixture of hydrochloric acid and glycine with a ratio of hydrochloric acid to glycine from about 1:10 to 10:1 as a mole ratio; and
   (C) citric acid.

7. The composition of claim 6, wherein the composition comprises from about 50 wt. % to about 99 wt. % water.

8. The composition of claim 6, wherein the composition comprises from 1 wt. % to 10 wt. % of the mixture of glycine and hydrochloric acid.

9. The composition of claim 6, wherein the composition comprises from 1 wt. % to 10 wt. % citric acid.

10. The composition of claim 6, wherein the composition has a pH from −1 to 6.5.

11. The composition of claim 6, wherein the composition is used to preserve animal feed with increased nutrition value.

12. The composition of claim 11, wherein the animal feed is hay or plant or grain sprouts.

13. A method of preserving an animal feed with increased nutrition value comprising treating the animal feed with a preservative composition of claim 6 for a time period from about 1 hour to about 2 weeks.

14. The method of claim 13, wherein the animal feed is hay or alfalfa or wheat sprouts.

15. The method of claim 13, wherein the method comprises treating the organic matter with the preservative composition in a ratio from 1:1 to 1000:1.

16. The method of claim 13, wherein the time period is from about 24 hours to about 5 days.

* * * * *